United States Patent [19]
Oldendorf et al.

[11] Patent Number: 5,602,889
[45] Date of Patent: Feb. 11, 1997

[54] DEVICE FOR FORMING X-RAY IMAGES

[75] Inventors: Frank Oldendorf; Heinz Haarmann; Anja Libera, all of Hamburg; Gerd Spitzmann, Pinneberg, all of Germany

[73] Assignee: U.S. Philips Corporation, New York, N.Y.

[21] Appl. No.: 514,522

[22] Filed: Aug. 14, 1995

[30] Foreign Application Priority Data

Aug. 13, 1994 [DE] Germany ............................ 44 28 779.8

[51] Int. Cl.$^6$ .............................. B41M 5/00; G03G 13/05
[52] U.S. Cl. ................................ 378/29; 378/28; 378/195
[58] Field of Search ...................... 378/28, 29, 31, 378/32, 193, 195, 197, 196, 189, 208

[56] References Cited

U.S. PATENT DOCUMENTS

| 4,975,935 | 12/1990 | Hillen et al. | 378/28 |
| 5,093,851 | 3/1992 | Schafer | 378/29 |

FOREIGN PATENT DOCUMENTS

| 4015113 | 5/1990 | Germany . | |

*Primary Examiner*—Don Wong
*Attorney, Agent, or Firm*—Jack D. Slobod

[57] ABSTRACT

A device for forming X-ray images, includes an X-ray source for generating an X-ray beam, a photoconductor for converting X-rays into a charge pattern, which photoconductor is provided on a rotationally symmetrically constructed rotatable carrier, a charging device for uniformly charging the surface of the rotating photoconductor prior to the X-ray exposure, a reading unit for converting the charge pattern on the surface of the rotating photoconductor into electric image values after an X-ray exposure, and a housing for the rotating parts which includes an area which is transparent to X-rays. The device enables X-ray images of a patient to be formed in at least one position other than the recumbent position in that the X-ray source can be positioned in different angular positions in an angular range about the axis of rotation, and that the area which is transparent to X-rays extends across such a part of the housing that the photoconductor can be exposed in any angular position of the X-ray source within the angular range.

20 Claims, 4 Drawing Sheets

DEVICE FOR FORMING X-RAY IMAGES

BACKGROUND OF THE INVENTION

1. Field of Invention

The invention relates to a device for forming X-ray images, comprising an X-ray source for generating an X-ray beam, a photoconductor for converting X-rays into a charge pattern, which photoconductor is provided on a rotationally symmetrically constructed rotatable carrier, a charging device for uniformly charging the surface of the rotating photoconductor prior to the X-ray exposure, a reading unit for converting the charge pattern on the surface of the rotating photoconductor into electric image values after an X-ray exposure, and a housing for the rotating parts which comprises an area transparent to X-rays.

2. Description of the Related Art

A device of this kind is known from DE-A 40 15 113. Therein, exposure is performed by an X-ray source which is arranged perpendicularly above the photoconductor. The patient is recumbent on a table top above the photoconductor. The table top and the part of the housing which is situated in the beam path therebelow and which encloses the rotating photoconductor are made of a material which is transparent to X-rays.

SUMMARY OF THE INVENTION

It is an object of the present invention to provide a device which allows for X-ray images to be formed of a patient in at least one position other than the recumbent position.

On the basis of a device of the kind set forth, this object is achieved in accordance with the invention in that the X-ray source can be positioned in different angular positions within an angular range about the axis of rotation and that the area which is transparent to X-rays extends across such a part of the housing that the photoconductor can be exposed from any angular position of the X-ray source that can be adjusted within said angular range.

Whereas only a single irradiation direction is possible in the known device, in the device in accordance with the invention the radiation direction can be varied in an angular range about the axis of rotation. This offers the advantage that the patient can be irradiated not only from above in the recumbent position but also in other positions; for example the patient can be irradiated laterally in the standing position. In the case of a stationary, perpendicular axis of rotation, this desired variation of the irradiation direction is not possible. The object can nevertheless be achieved by adapting the axis of rotation of the carrier to the desired exposure direction, i.e. adjusting the axis of rotation so that it extends horizontally in the case of X-ray exposures from above and vertically in the case of X-ray exposures from the side. In a preferred embodiment of the invention the axis of rotation of the rotationally symmetrically constructed carrier extends in the horizontal direction. A device for pivoting the carrier in order to adjust its axis of rotation can then be dispensed with.

In a further preferred embodiment the angular range amounts to at least 90°. The most frequently required X-ray images of the patient can then be formed directly perpendicularly from above in the recumbent position and in the horizontal direction in the standing position. For example, X-ray images of the vertebral column in the loaded and in the non-loaded state can thus be formed consecutively in one apparatus.

In a further embodiment of the invention, the device for charging the surface of the photoconductor prior to the exposure and the unit for reading the X-ray image are arranged in such a manner that they are situated outside the beam path between the X-ray source and the photoconductor in any possible angular position of the X-ray source.

In a further embodiment of the invention, the housing which encloses the rotationally symmetrically constructed carrier and in which this carrier is journalled consists of flat walls which are arranged substantially at right angles to one another, thus allowing for a simple construction. Two neighbouring walls, preferably the upper horizontal wall and a side wall, are made of a material which is transparent to X-rays.

A further embodiment is provided with at least two sensor devices which are known per se and which serve to detect the charge intensity being built up on the surface of the photoconductor during the exposure. These sensor devices are arranged in such a manner that each time one device for a given radiation direction is present within the beam path between the X-ray source and the photoconductor. A further embodiment also comprises a control circuit which automatically switches off the X-rays when adequate exposure of the photoconductor is reached as monitored by one of the sensor devices. This means that the patient is exposed only to the X-ray dose required for a given, desired image resolution. A control circuit provided in a further embodiment selects the sensor device which is situated in the beam path from among the sensor devices provided, which selection is dependent on the angular position of the X-ray source prior to the exposure, and activates this sensor device. As a result, the operators need not carry out this task so that faulty operation due to incorrect or no selection of a sensor device is prevented, which again benefits the safety of the patient.

In a preferred embodiment there are provided means for adjusting the height of the housing in order to enable adaption of its level to the size and/or the position of the patient. Furthermore, there may be provided a control circuit which automatically moves the X-ray source to the appropriate position in conformity with the height of the housing and the desired radiation direction. This enables simple operation of the overall device and also reduces the probability of incorrect exposure, for example due to incorrect adjustment of the irradiation direction or an incorrect distance between the X-ray source and the photoconductor.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
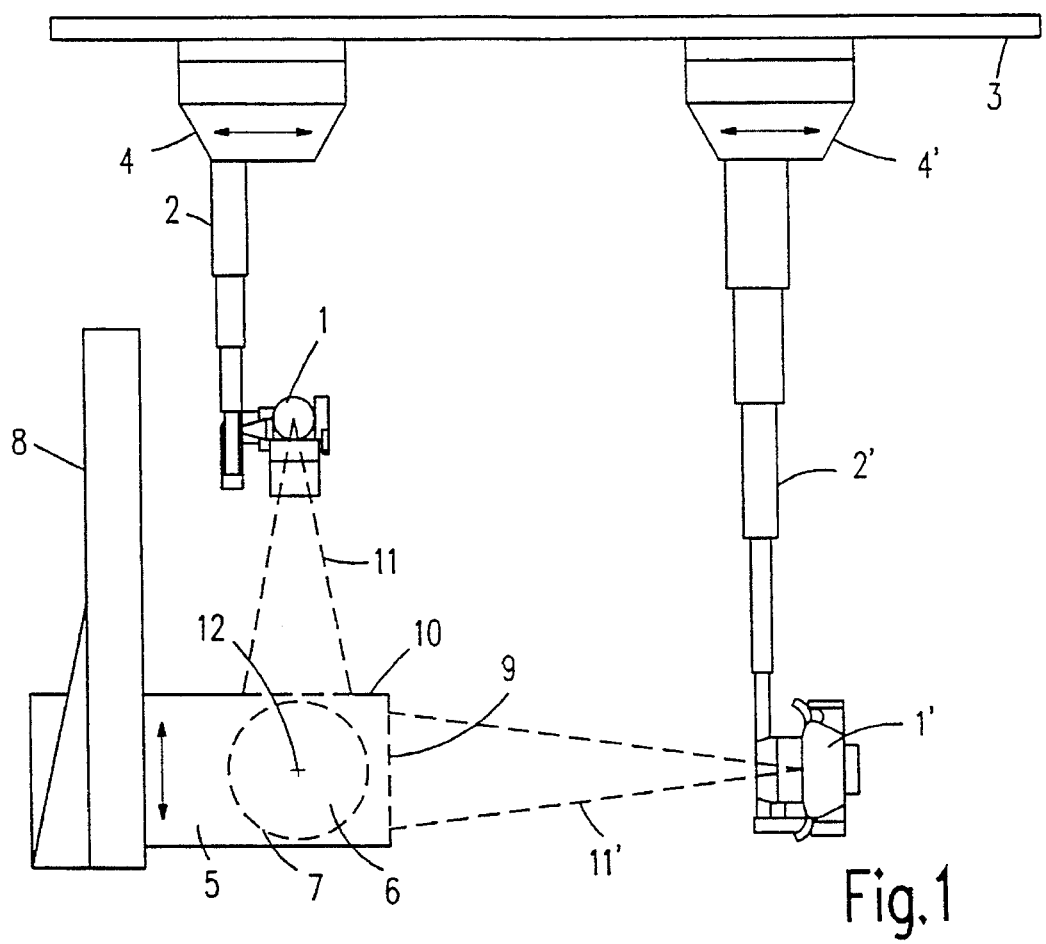
FIG. 1 shows an X-ray apparatus in accordance with the invention.

The reference 1 in FIG. 1 denotes an X-ray source which is mounted so as to be pivotable in an arbitrary direction on a vertical telescopic arm 2 of variable length. Via a rail 3 attached to the ceiling, the telescopic arm 2, mounted in a rail runner 4, can be positioned in the horizontal direction. The components denoted by the references 1, 2 and 4 are denoted by the references 1', 2' and 4' in the position which is shown at the right for the horizontal irradiation direction. The housing 5, in which the rotationally symmetrically constructed carrier 6 on which the photoconductor 7 is provided is journalled, is connected to a base stand 8. The axis of rotation 12, about which the carrier 6 can be rotated by way of a drive (not shown), extends perpendicularly to the plane of drawing and in the horizontal direction. The housing 5 is formed by mutually perpendicularly arranged flat walls, two adjoining walls thereof, i.e. preferably the side wall 9 facing the base stand 8 and the upper horizontal angle wall 10, being made of a material which is transparent to X-rays but not to visible light, for example aluminium; this transparent area can be situated in the radiation beam 11 between the X-ray source 1 and the photoconductor 7 in any feasible position of the X-ray source 1.

Figure 2:
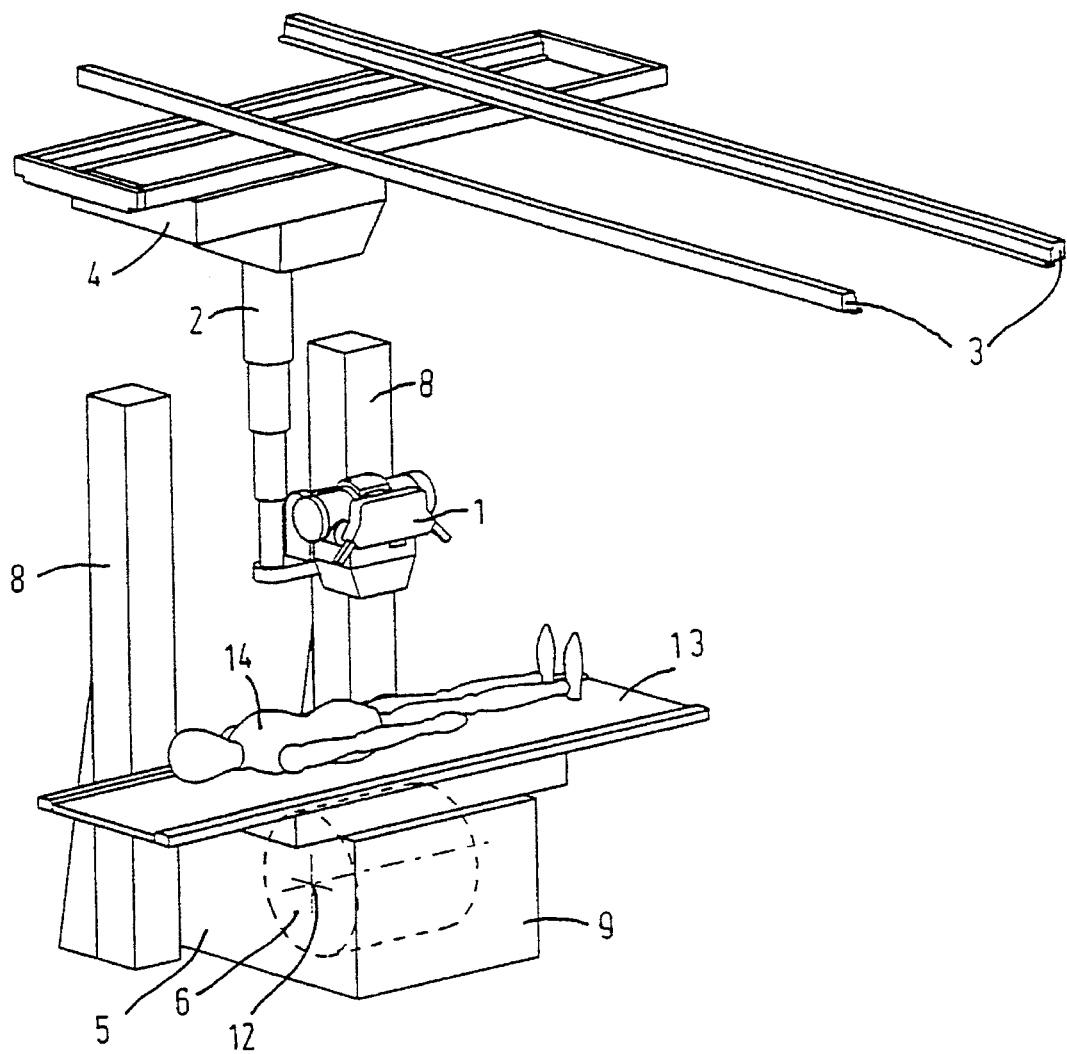
FIG. 2 shows a device for forming an X-ray image of a recumbent patient, exposure taking place from above with a perpendicular irradiation direction.
Figure 3:
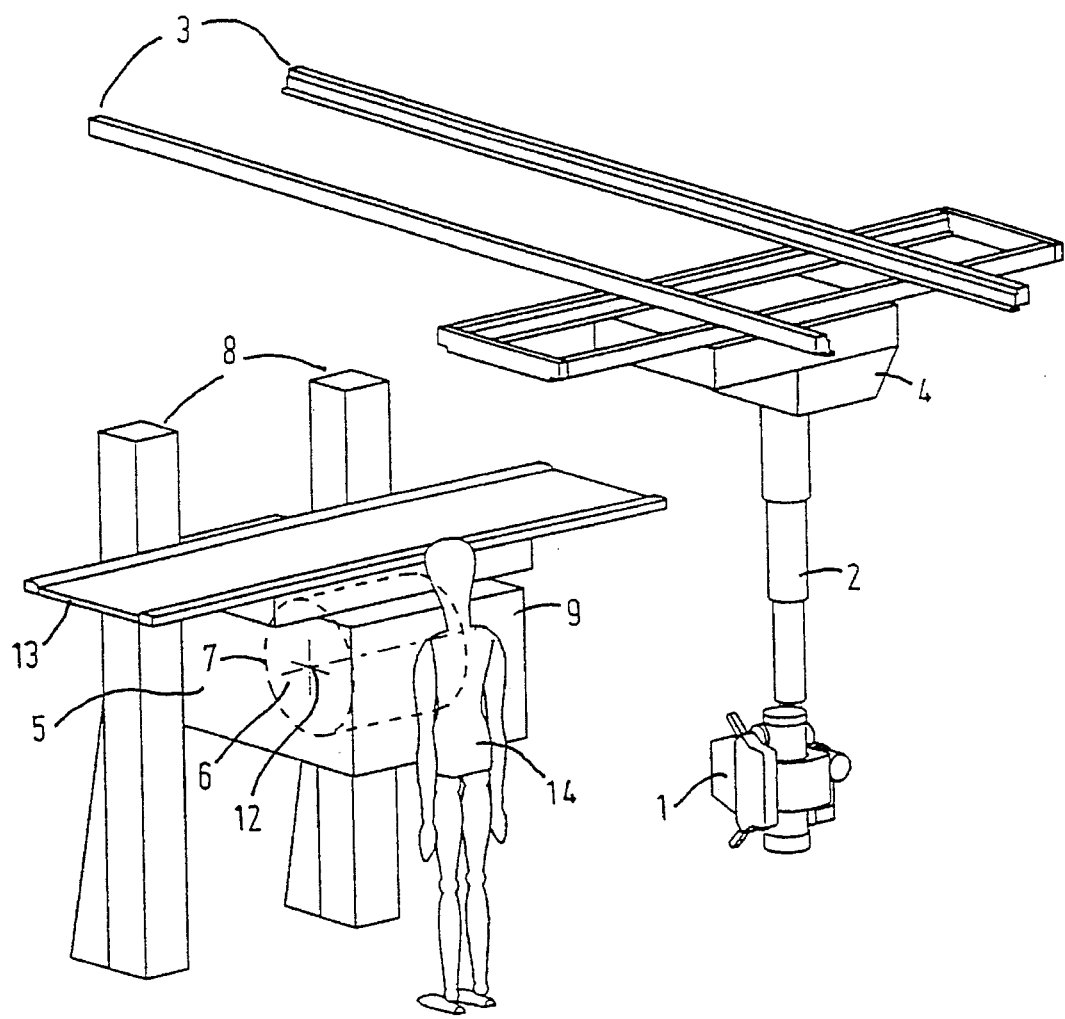
FIG. 3 shows a device for forming an X-ray image of a standing patient from the side with a horizontal irradiation direction.
Figure 4:
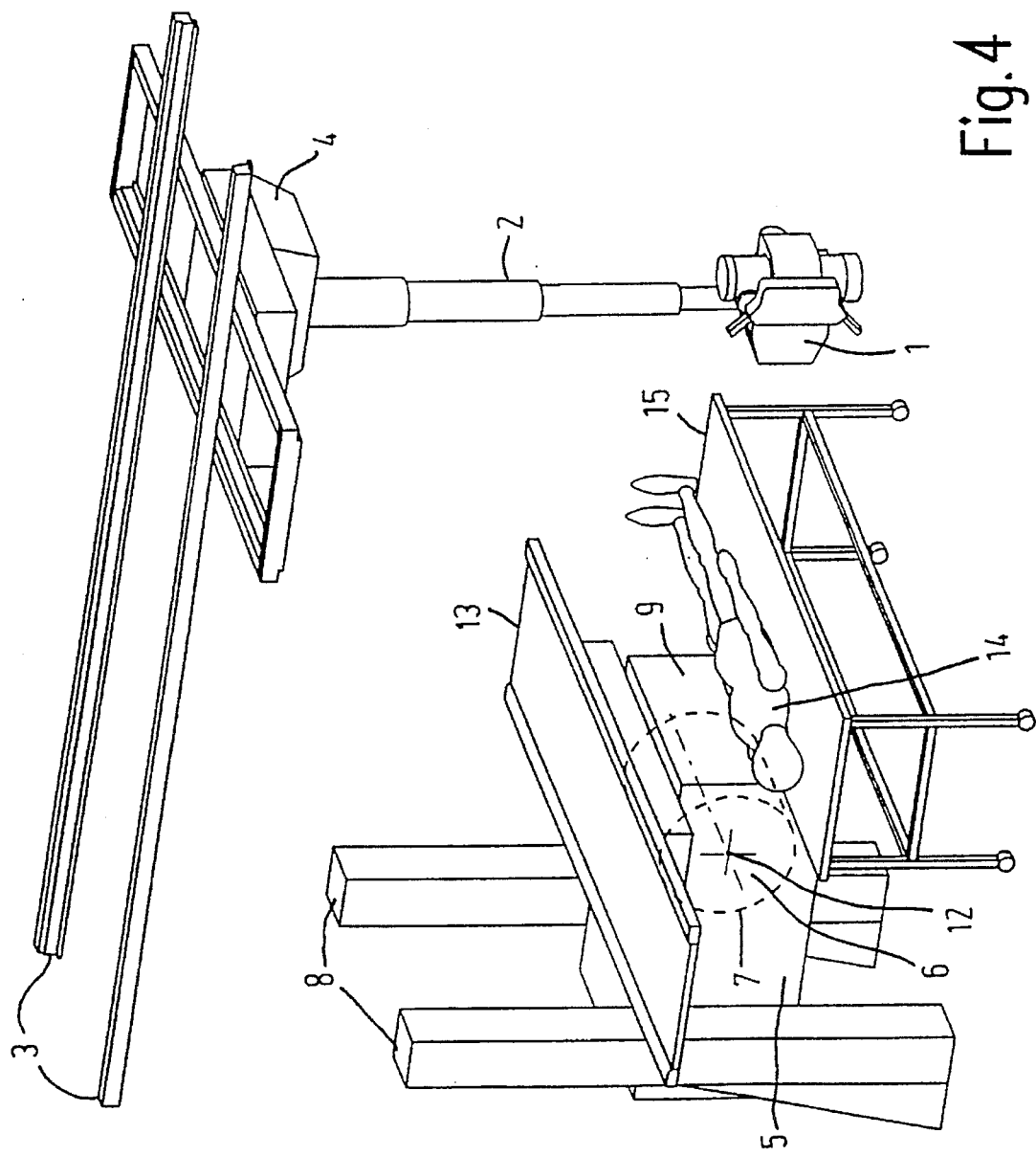
FIG. 4 shows a device for forming an X-ray image of a patient, positioned on an additional table, from the side with a horizontal irradiation direction.

The FIGS. 2 to 4 are perspective views of devices for forming X-ray images in different positions of a patient.

FIG. 2 shows the device for forming an image of a recumbent patient 14. In order to facilitate the positioning of the patient 4 on the table top 13, or to facilitate the operator's work in arranging the patient 14 on the table top 13, the housing 5 with the table top 13 mounted thereon can be adjusted to its lowest position on the base stand 8 which is defined by the diameter of the cylindrical carrier 6. In order to move the part of the body to be imaged into the beam path 11, the table top 13 can be displaced horizontally in the direction parallel to the axis of rotation 12.

FIG. 3 shows the device for forming an X-ray image of the thorax of a patient standing in front of the housing 5. Using a height adjusting device (not shown), the height of the housing 5 on the base stand 8 is adjusted in conformity with the length of the patient 14. Preferably, a control device (not shown) automatically adjusts the X-ray source 1 to the same height for the desired horizontal irradiation direction. This arrangement of the X-ray source 1 also enables the imaging of other parts of the body, such as the head or a knee, since the housing 5 and the X-ray source 1 can then be adjusted to the appropriate height.

As is shown in FIG. 4 for the same irradiation direction X-ray images can also be formed by moving the patient 14 to the correct exposure position by means of an accessory, i.e. a table 15 in the case shown. Examples of such accessories are (not shown) a chair or a rest for, for example a foot.

Figure 5:
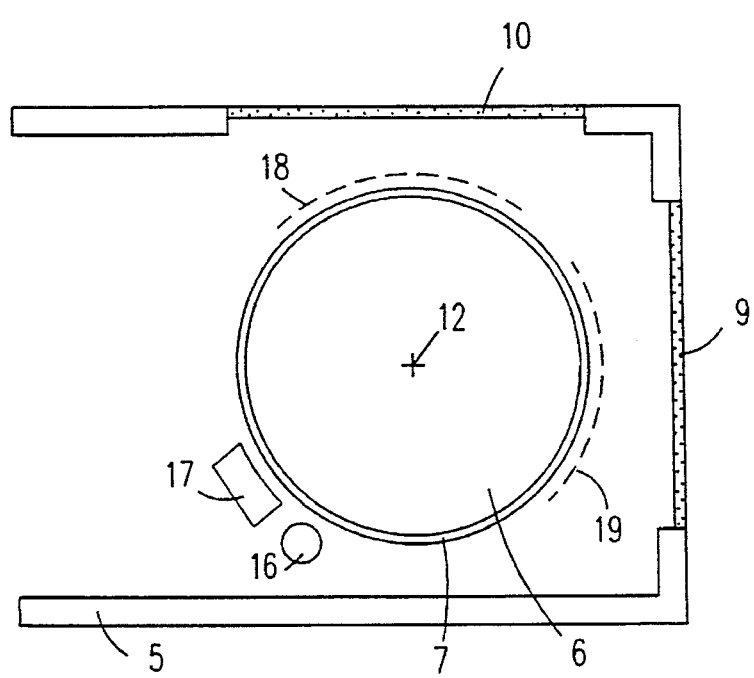
FIG. 5 is a sectional view of the housing with an effective arrangement of a charging and reading unit as well as the sensor devices.

FIG. 5 is a partial sectional view of the housing 5 with the cylindrical carrier 6, illustrating the position of the charging device 16, the reading unit 17 and two sensor devices 18 and 19. In a special embodiment comprising two X-ray transparent windows 9 and 10 two sensor devices 18 and 19 are arranged in the radiation beam between the windows 9 and 10 and the photoconductor 7. In the case of an X-ray exposure, for example perpendicularly from above with a vertical irradiation direction, the sensor device 18 is activated during the exposure. This device measures the intensity of the charge on the surface of the photoconductor 7 and when the exposure suffices the X-ray source is switched off by means of a control device in order to ensure that the patient is not exposed to the X-rays longer than necessary. The charging device 16 and the reading unit 17 are arranged in such a location that they are not situated in the beam path between the X-ray source 1 and the photoconductor 7. In the case shown this is the area to the side of the carrier 6 in the bottom region which is remote from the windows 9 and 10.

We claim:

1. A device for forming X-ray images, comprising an X-ray source for generating an X-ray beam, a photoconductor for converting X-rays into a charge pattern, which photoconductor is provided on a rotationally symmetrically constructed rotatable carrier, a charging device for uniformly charging the surface of the rotating photoconductor prior to the X-ray exposure, a reading unit for converting the charge pattern on the surface of the rotating photoconductor into electric image values after an X-ray exposure, and a housing for the rotating parts which comprises an area transparent to X-rays, characterized in that the X-ray source can be positioned in different angular positions within an angular range about the axis of rotation and that the area which is transparent to X-rays extends across such a part of the housing that the photoconductor can be exposed from any angular position of the X-ray source that can be adjusted within said angular range.

2. A device as claimed in claim 1, characterized in that the axis of rotation of the rotationally symmetrically constructed carrier extends in the horizontal direction.

3. A device as claimed in claim 1, characterized in that the angular range amounts to at least 90°.

4. A device as claimed in claim 2, characterized in that the angular range extends from a perpendicular direction through the axis of rotation as far as a horizontal direction through said axis of rotation.

5. A device as claimed in claim 1, characterized in that the charging device and the reading device are adjacently arranged within an angular range relative to the carrier which is situated outside the area transparent to X-rays.

6. A device as claimed in claim 1, characterized in that the housing comprises walls which are arranged substantially at right angles to one another, two neighbouring walls being constructed as windows which are transparent to X-rays.

7. A device as claimed in claim 1, characterized in that at least two sensor devices are provided in different angular positions in order to detect the intensity of the charge on the surface of the photoconductor and that a control circuit is also provided for automatically switching off the X-rays when a limit value of the charge intensity is reached.

8. A device as claimed in claim 7, characterized in that a further control circuit is provided to activate the sensor device present in the beam path in dependence on the angular position of the X-ray source.

9. A device as claimed in claim 1, characterized in that means are provided for adjusting the height of the housing.

10. A device as claimed in claim 9, characterized in that a control device is provided so as to adjust the X-ray source automatically to the appropriate position in conformity with the height of the housing and the desired irradiation direction.

11. A device as claimed in claim 2, characterized in that the angular range amounts to at least 90°.

12. A device as claimed in claim 2, characterized in that the charging device and the reading device are adjacently arranged within an angular range relative to the carrier which is situated outside the area transparent to X-rays.

13. A device as claimed in claim 3, characterized in that the charging device and the reading device are adjacently arranged within an angular range relative to the carrier which is situated outside the area transparent to X-rays.

14. A device as claimed in claim 4, characterized in that the charging device and the reading device are adjacently arranged within an angular range relative to the carrier which is situated outside the area transparent to X-rays.

15. A device as claimed in claim 2, characterized in that the housing comprises walls which are arranged substantially at right angles to one another, two neighboring walls being constructed as windows which are transparent to X-rays.

16. A device as claimed in claim 3, characterized in that the housing comprises walls which are arranged substantially at right angles to one another, two neighboring walls being constructed as windows which are transparent to X-rays.

17. A device as claimed in claim 2, characterized in that at least two sensor devices are provided in different angular positions in order to detect the intensity of the charge on the surface of the photoconductor and that a control circuit is also provided for automatically switching off the X-rays when a limit value of the charge intensity is reached.

18. A device as claimed in claim 3, characterized in that at least two sensor devices are provided in different angular positions in order to detect the intensity of the charge on the surface of the photoconductor and that a control circuit is also provided for automatically switching off the X-rays when a limit value of the charge intensity is reached.

19. A device as claimed in claim 17, characterized in that a further control circuit is provided to activate the sensor device present in the beam path in dependence on the angular position of the X-ray source.

20. A device as claimed in claim 2, characterized in that means are provided for adjusting the height of the housing.

* * * * *